United States Patent
Herr et al.

(10) Patent No.: US 8,212,010 B2
(45) Date of Patent: Jul. 3, 2012

(54) SPHINGOSINE 1-PHOSPHATE ANTAGONISM

(75) Inventors: Deron R. Herr, San Diego, CA (US); Greg L. Harris, Encinitas, CA (US)

(73) Assignee: Expression Drug Designs, LLC, Cardiff, CA (US)

( * ) Notice: Subject to any disclaimer, the term of this patent is extended or adjusted under 35 U.S.C. 154(b) by 0 days.

(21) Appl. No.: 12/391,664

(22) Filed: Feb. 24, 2009

(65) Prior Publication Data

US 2009/0226453 A1 Sep. 10, 2009

Related U.S. Application Data

(60) Provisional application No. 61/031,111, filed on Feb. 25, 2008.

(51) Int. Cl.
*C07K 16/00* (2006.01)
*C12N 15/07* (2006.01)
*G01N 33/53* (2006.01)

(52) U.S. Cl. .................. 530/388.1; 530/391.7; 435/451; 435/7.1

(58) Field of Classification Search .......................... None
See application file for complete search history.

(56) References Cited

U.S. PATENT DOCUMENTS

| | | | | |
|---|---|---|---|---|
| 6,130,067 | A * | 10/2000 | Tsui ............................. | 435/69.1 |
| 6,340,461 | B1 * | 1/2002 | Terman ........................ | 435/69.1 |
| 6,344,542 | B1 | 2/2002 | Tsui | |
| 6,485,922 | B1 | 11/2002 | Erickson et al. | |
| 7,063,966 | B2 | 6/2006 | Shankar et al. | |
| 7,064,217 | B2 | 6/2006 | Macdonald | |
| 7,208,502 | B2 | 4/2007 | Solow-Cordero | |
| 7,241,812 | B2 | 7/2007 | Saha | |
| 2002/0155512 | A1 | 10/2002 | Liao et al. | |
| 2003/0113798 | A1 | 6/2003 | Burmer et al. | |
| 2005/0137185 | A1 * | 6/2005 | Lee et al. ..................... | 514/217 |

FOREIGN PATENT DOCUMENTS

| | | |
|---|---|---|
| EP | 1798226 A1 | 6/2007 |
| EP | 1826197 A1 | 8/2007 |
| EP | 1988081 A1 | 11/2008 |
| EP | 1988083 A1 | 11/2008 |
| WO | WO-99/60019 A1 | 11/1999 |
| WO | WO-2008/070344 A2 | 6/2008 |

OTHER PUBLICATIONS

Davis M D et al., "Sphingosine 1-Phosphate Analogs as Receptor Antagonists"; Journal of Biological Chemistry, American Society of Biolochemical Biologists, Birmingham, USA vol. 280, No. 11, Dec. 8, 2004, pp. 9833-9841; XP002395963.

NCBI Document Q99500. RecName: Full=Sphingosine 1-phosphate receptor 3; Short=S1P receptor 3; Short=S1P3; AtlName: Full=Sphingosine 1-phosphate receptor Edg-3; Short=S1P receptor Edg-3; AltName: FullmEndothelial differentiation G-protein coupled receptor 3. Feb. 16, 2004 found at <http://www.ncbi.nim.nih.gov/protein/42560554>.

Elrod et al., A study on the correlation of G-protein-coupled receptor types with amino acid composition. Protein Engineering vol. 15, No. 9, pp. 713-715, 2002, entire document.

Dolezalova, Hana et al., "Biochemical Regulation of Breast Cancer Cell Expression of S1P2 (Edg-5) and S1P3 (Edg-3) G Protein-Coupled Receptors for Sphingosine 1-Phosphatase"; *Journal of Cellular Biochemistry* 88:732-743 (2003); Wiley-Liss Inc.

Döll, Frank et al., "The epidermal growth factor stimulates sphingosine kinase-1 expression and activity in the human mammary carcinoma cell line MCF7"; *Biochimica et Biophysica Acta* 1738 (2005) 72-81.

Goetzl, Edward et al., "Dual Mechanisms for Lysophospholipid Induction of Proliferation of Human Breast Carcinoma Cells"; *Cancer Research* 59, 4732-4737, Sep. 15, 1999.

Herr, D.R. et al., "Effects of LPA and S1P on the Nervous System and Implications for Their Involvement in Disease"; *Current Drug Targets* 2007, 8, 155-167.

Herr, Deron R. et al., Sphingosine 1-Phosphate (S1P) Signaling is Required for Maintenance of Hair Cells Mainly via Activation of S1P2; *The Journal of Neuroscience*, Feb. 7, 2007, 27(6):1474-1478.

LaMontagne, Kenneth et al., "Antagonism of Sphingosine-1 Phosphate Receptors by FTY720 Inhibits Angiogenesis and Tumor Vascularization", *Cancer Res* 2006: (1). Jan. 1, 2006.

Nava, Victor E. et al., "Sphingosine Kinase Type 1 Promotes Estrogen-Dependent Tumorigenesis of Breast Cancer MCF-7 Cells", *Experimental Cell Research* 281, 115-127 (2002).

Niessen, Frank et al., "Dendritic cell PAR1-S1P3 signalling couples coagulation and inflammation", *Nature*, Letters Feb. 27, 2008; Nature Publishing Group.

Sarkar, Sukumar et al., "Sphingosine kinase 1 is required for migration, proliferation and survival of MCF-7 human breast cancer cells"; *FEBS Letters* 579 (2005) 5313-5317.

Sukocheva, Olga et al., "Estrogen transactivates EGFR via the sphingosine 1-phosphate receptor Edg-3: the role of sphingosine kinase-1"; *JCB Article*, vol. 173, No. 2, 2008., pp. 301-310.

European Office Action; Application No. 09714655.9-2107; Aug. 7, 2011, 10 pages.

* cited by examiner

*Primary Examiner* — Lei Yao

(74) *Attorney, Agent, or Firm* — Arent Fox, LLP; Patricia Granados

(57) ABSTRACT

Materials and Method for treating cancer and screening for anti-neoplastic agents are provided. These materials and methods can include sphingosine 1-phosphate antagonists that bind to sphingosine-1 phosphate receptor subtype 3. Antibodies and aptamers that selectively bind to an epitope in the extracellular loop between transmembrane domains two and three of sphingosine-1-phosphate receptor subtype 3 are provided.

12 Claims, No Drawings

SPHINGOSINE 1-PHOSPHATE ANTAGONISM

This application claims priority to U.S. Provisional Patent Application No. 61/031,111, filed Feb. 25, 2008, incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Nov. 17, 2010, is named 30163002.txt and is 909 bytes in size.

BACKGROUND OF THE INVENTION

Sphingosine 1-phosphate (S1P) is a small signaling lipid molecule that is present in low concentrations in the plasma membrane of nearly all eukaryotic cells and at high concentrations in serum. S1P is generated by the phosphorylation of sphingosine by sphingosine kinase (SphK) and acts on a family of five known S1P-selective G protein-coupled receptors (the five subtypes designated as S1P1, S1P2, S1P3, S1P4, and S1P5). These receptors couple to a number of G-proteins and down-stream effectors to elicit a variety of cellular responses. The responses vary depending on the expression profile of the receptors and effectors, but notably include proliferation, survival, and cytoskeletal rearrangement.

S1P and its receptors have been implicated as playing a role in cancer. Not all receptor subtypes appear to play an equal role in cancer and blocking some subtypes could elicit harmful side effects and might even promote cancer. For example, FTY720 is a broad-spectrum S1P receptor inverse agonist that has been reported to effectively inhibit four of the five known receptors (with the exception of S1P2) by stable internalization. Administration of FTY720 has been shown to inhibit angiogenesis and subsequent growth in a tumor transplant model. This effect is mediated through the functional antagonism of S1P1 and S1P3. S1P3 is also known as EDG3, EDG-3, S1PR3, and LPB3. An unfortunate side-effect of S1P1 antagonism is marked lymphopenia and immunosuppression. Accordingly, there is a significant need in the art for S1P3 selective antagonists that would retain the tumor-suppressive and anti-angiogenic properties of FTY720 without the immunosuppression associated with S1P1 antagonism.

Although there are many chemotherapeutic medications on the market, few, if any, of these medications appear to be sufficient to consistently treat cancer in patients. Accordingly, it is a further object of this invention to identify anti-neoplastic agents that can enhance the efficacy of existing chemotherapeutics.

Coagulation is one of the principal features of systemic inflammatory response syndromes in bacterial sepsis and viral hemorrhagic fevers. While some anticoagulants can show efficacy in severe sepsis with disseminated intravascular coagulation, there remains a considerable need for new therapeutics in these areas. New methods of and agents for preventing disseminated intravascular coagulation are sought.

SUMMARY OF THE INVENTION

An isolated sphingosine-1-phosphate (S1P) antagonist that selectively binds to an epitope in the extracellular loop between transmembrane domains two and three of sphingosine-1-phosphate receptor subtype 3 (S1P3) is provided by the invention. In some embodiments, the amino acid sequence KKTFSLSPTVWFLREG (SEQ ID NO: 1) comprises the epitope. Examples of antagonist types include antibodies and aptamers. Examples of antibodies include polyclonal antibodies, monoclonal antibodies, single-chain antibodies, diabodies, antibody fragments, and immunoconjugates in which the antibody or fragment is conjugated to a functional agent. Examples of functional agents include detectable markers, anti-neoplastic agents, and cytotoxic agents generally. Hybridomas producing antibodies of the invention are also provided. The antagonist itself can be an anti-neoplastic agent. Compositions comprising the antagonist and one or more (further) anti-neoplastic agents are also provided by the invention. Examples of anti-neoplastic agents include an estrogen receptor binder, antimetabolites, taxanes, anthracyclines, progestins, megestrols, aromatase inhibitors, tyrosine kinase inhibitors, and epidermal growth factor inhibitors.

A method of treating a cancer cell in a subject is provided by the invention. The method comprising administering an effective amount of a first anti-neoplastic agent comprising an isolated sphingosine-1-phosphate (S1P) antagonist that selectively binds to an epitope in the extracellular loop between transmembrane domains two and three of sphingosine-1-phosphate receptor subtype 3 (S1P3) thereby treating the cancer cell in the subject. The cancer treatment can comprise antagonizing one or more of the following: proliferation of the cell, remodeling of the cell, migration of the cell, invasion by the cell, and survival of the cell. The cancer cell treated can be of any suitable cancer cell type. For example, the cancer cell can comprise one or more of a breast cancer cell, a colorectal cancer cell, a cervical cancer cell, an endometrial cancer cell, an ovarian cancer cell, a prostate cancer cell, a lung cancer cell, a glioblastoma cell. The method can comprise administering a second anti-neoplastic agent, separately or in combination, wherein the first anti-neoplastic agent enhances the second anti-neoplastic agent or vice versa. In some embodiments, the enhancement is synergistic. When administering first and second anti-neoplastic agents, a composition of the invention can be administered.

A method for identifying a test agent that enhances the efficacy of an anti-neoplastic agent in antagonizing a neoplastic cell is provided by the invention. The method can comprise the following steps. A first sample comprising a neoplastic cell is provided. A second sample comprising a neoplastic cell is provided. The type(s) of neoplastic cell in the first and second samples can be the same. The anti-neoplastic agent is applied to the first and second samples. The test agent is applied to the second sample. The first and second samples are assayed for an anti-neoplastic effect. The test agent is identified as an enhancer or not an enhancer based on the effect measured in the second sample compared to the effect measured in the first sample. The test agent employed is an isolated sphingosine-1-phosphate (S1P) antagonist that selectively binds to an epitope in the extracellular loop between transmembrane domains two and three of sphingosine-1-phosphate receptor subtype 3 (S1P3). In some embodiments, the enhancement is synergistic. Examples of anti-neoplastic results that can be measured include cell stabilization, cell death, growth inhibition, cytoskeletal stabilization, and migration inhibition.

Use of an isolated sphingosine-1-phosphate (S1P) antagonist that selectively binds to an epitope in the extracellular loop between transmembrane domains two and three of sphingosine-1-phosphate receptor subtype 3 (S1P3) to treat a cancer cell in a subject is provided by the invention. The invention also provides use of an isolated sphingosine-1-phosphate (S1P) antagonist that selectively binds to an epitope in the extracellular loop between transmembrane domains two and three of sphingosine-1-phosphate receptor subtype 3 (S1P3) for the manufacture of a medicament to treat cancer.

Kits employing compounds and compositions of the invention and that can be employed in the uses and methods of the invention are provided. A kit comprising at least two elements is provided by the invention. First, the kit includes an isolated sphingosine-1-phosphate (S1P) antagonist that selectively binds to an epitope in the extracellular loop between transmembrane domains two and three of sphingosine-1-phosphate receptor subtype 3 (S1P3). Second, the kit includes an anti-neoplastic agent.

Methods of preventing and treating systemic inflammation and the pathological coagulation associated with bacterial sepsis, viral hemorrhagic fever, systemic inflammatory response syndromes, and other conditions are provided. For example, a method of preventing or treating disseminated intravascular coagulation in a subject is provided. The method can comprise administering an effective amount of a first anti-coagulation agent comprising an isolated sphingosine-1-phosphate (S1P) antagonist that selectively binds to an epitope in the extracellular loop between transmembrane domains two and three of sphingosine-1-phosphate receptor subtype 3 (S1P3) thereby preventing disseminated intravascular coagulation in the subject. Use of an isolated sphingosine-1-phosphate (S1P) antagonist that selectively binds to an epitope in the extracellular loop between transmembrane domains two and three of sphingosine-1-phosphate receptor subtype 3 (S1P3) for the manufacture of a medicament to prevent or treat disseminated intravascular coagulation as well as associated conditions is also provided.

Methods of preventing or treating any condition associated with sphingosine-1-phosphate receptor subtype 3 (S1P3) signaling are provided using the antagonists of the invention. Kits and compositions for use with such methods are also provided.

DETAILED DESCRIPTION OF THE PREFERRED EMBODIMENTS

The present invention provides an isolated sphingosine-1-phosphate (S1P) antagonist that selectively binds to an epitope in the extracellular loop between transmembrane domains two and three of sphingosine-1-phosphate receptor subtype 3 (S1P3). The amino acid sequence KKTFSLSPTVWFLREG (SEQ ID NO: 1) can comprise the epitope. The antagonist can take any suitable form. The antagonist binds to sphingosine-1-phosphate receptor subtype 3 (S1P3) such that the binding of S1P to the receptor is completely or partially abolished. The antagonist can be a competitive inhibitor, a noncompetitive inhibitor or both of S1P. The antagonist can be a reversible inhibitor, an irreversible inhibitor or both of S1P. In some embodiments, the S1P antagonist is an antagonist or partial antagonist of the S1P3 receptor. In some embodiments, the S1P antagonist is an agonist or partial agonist of the S1P3 receptor.

An isolated molecule is one that has been removed from the environment in which it naturally occurs. An isolated molecule can be returned to the environment in which it occurs and still be considered an isolated molecule as it had been previously separated from its natural environment. Isolated molecules include isolated nucleic acids, isolated proteins, isolated polypeptides, and isolated antibodies.

The S1P antagonist can comprise an antibody or a polypeptide comprising an antigen-binding fragment of the antibody. In some embodiments, the antibody is a chimeric antibody. In some embodiments, the antibody is a humanized antibody. In some embodiments, the antibody is a completely humanized antibody. The antibody can be a monoclonal antibody. The antibody can be a polyclonal antibody. In some embodiments, the antibody is a single-chain antibody. The antibody can be a diabody or a monovalent antibody.

The S1P antagonist can comprise an aptamer. In some embodiments, the aptamer comprises a nucleic acid. The aptamer can comprise RNA. The aptamer can comprise DNA. Aptamers comprising nucleic acids can comprise natural and/or modified (non-natural) nucleotides. The aptamer can comprise an amino acid.

The S1P antagonist, in addition to being able to bind S1P3, can have one or more additional attributes. For example, it can bind or be operatively associated with one or more molecules or atoms. These molecules or atoms can comprise a cell toxin and/or render the antagonist detectable by one or more means.

The invention provides compositions that comprise one or more antagonist of the invention. These compositions can further comprise one or more anti-neoplastic agents. This anti-neoplastic agent is in addition to the S1P3 inhibitor itself, which can also be a anti-neoplastic agent. An anti-neoplastic agent is an agent that can be used in any suitable manner to treat and/or assist in the treatment of a cancer cell. The compositions can comprise one or more pharmaceutically acceptable excipient. In some embodiments, the anti-neoplastic agent of the composition binds to an estrogen receptor. For example, anti-neoplastic agents that bind an estrogen receptor can include tamoxifen, toremifene, raloxifene, clomiphene, any prodrug thereof, any salt thereof, and any combination thereof. In some embodiments, the anti-neoplastic agent of the composition is an antimetabolite, a prodrug thereof, a salt thereof, or any combination thereof. For example, an antimetabolite can comprise methotrexate, capecitabine, cladribine, cytarabine, fludarabine, fluorouracil, gemcitabine, mercaptopurine, thioguanine, any prodrug thereof, any salt thereof, and any combination thereof. In some embodiments, the anti-neoplastic agent of the composition is a taxane, a prodrug, a salt thereof, or any combination thereof. For example, the taxane, can comprise paclitaxel, docetaxel, any prodrug thereof, any salt thereof, and any combination thereof. In some embodiments, the anti-neoplastic agent of the composition is an anthracycline, a salt thereof, a prodrug thereof, or any combination thereof. For example, the anthracycline can comprise doxorubicin, daunorubicin, idarubicin, epirubicin, any prodrug thereof, any salt thereof, and any combination thereof. In some embodiments, the anti-neoplastic agent of the composition is a progestin, a prodrug thereof, a salt thereof, or any combination thereof. For example, the progestin can comprise megestrol, a prodrug thereof, a salt thereof, or any combination thereof. In some embodiments, the anti-neoplastic agent of the composition is an aromatase inhibitor, a prodrug thereof, a salt thereof, or any combination thereof. For example, the aromatase inhibitor can comprise aminoglutethimide, anastrozole, letrozole, exemestane, any prodrug thereof, any salt thereof, any combination thereof. In some embodiments, the anti-neoplastic agent is a tyrosine kinase inhibitor. In some embodiments, the anti-neoplastic agent of the composition binds to an epidermal growth factor receptor. For example, the anti-neoplastic agent can comprise gefitinib, cetuximab, lapatinib, erlotinib, trastuzumab, any prodrug thereof, any salt thereof, and any combination thereof.

Methods of preventing or treating any condition associated with sphingosine-1-phosphate receptor subtype 3 (S1P3) signaling are provided using the antagonists of the invention.

Kits and compositions for use with such methods are also provided.

A method of treating a cancer cell in a subject is provided by the invention. The method comprises administering an effective amount of a first anti-neoplastic agent comprising an isolated sphingosine-1-phosphate (S1P) antagonist that selectively binds to an epitope in the extracellular loop between transmembrane domains two and three of sphingosine-1-phosphate receptor subtype 3 (S1P3) thereby treating the cancer cell in the subject. The cancer treatment can comprise antagonizing one or more of the following: proliferation of the cell, remodeling of the cell, migration of the cell, invasion by the cell, and survival of the cell. The cancer cell treated can be of any suitable cancer cell type. For example, the cancer cell can comprise one or more of a breast cancer cell, a colorectal cancer cell, a cervical cancer cell, an endometrial cancer cell, an ovarian cancer cell, a prostate cancer cell, a lung cancer cell, a glioblastoma cell. The method of treatment can have anti-angiogenic effects.

The subject treated in accordance with the invention can have been diagnosed with a cancer or an increased susceptibility for a cancer. Any cancer susceptible to the treatments of the invention can be treated. As used herein, the term "cancer" is meant any malignant growth or tumor caused by abnormal and uncontrolled cell division that may spread to other parts of the body through the lymphatic system or the blood stream. The cancer can be, for example, breast cancer, prostate cancer, lung cancer, colon cancer, rectal cancer, urinary bladder cancer, non-Hodgkin lymphoma, melanoma, renal cancer, pancreatic cancer, cancer of the oral cavity, pharynx cancer, ovarian cancer, thyroid cancer, stomach cancer, brain cancer, multiple myeloma, esophageal cancer, liver cancer, cervical cancer, larynx cancer, cancer of the intrahepatic bile duct, acute myeloid leukemia, soft tissue cancer, small intestine cancer, testicular cancer, chronic lymphocytic leukemia, Hodgkin lymphoma, chronic myeloid cancer, acute lymphocytic cancer, cancer of the anus, anal canal, or anorectum, cancer of the vulva or cancer of the neck, gallbladder, or pleura, malignant mesothelioma, bone cancer, cancer of the joints, hypopharynx cancer, cancer of the eye, cancer of the nose, nasal cavity, neck, or middle ear, nasopharynx cancer, ureter cancer, peritoneum, omentum, or mesentery cancer, or gastrointestinal carcinoid tumor. The cancer can be a tumor. The tumor can be a solid tumor. The cancer can be a hematogenous malignancy. The cancer can be a leukemia. In some embodiments, the leukemia is an acute lymphoblastic leukemia. The cancer can be an ovarian cancer. In some embodiments, the ovarian cancer is an ovarian adenocarcinoma, ovarian carcinoma, clear cell ovarian cancer, endometrioid ovarian cancer, mucinous ovarian cancer, serous ovarian cancer, mixed ovarian cancer, or any combination thereof. The cancer can be a pancreatic cancer. In some embodiments, the pancreatic cancer is a pancreatic adenocarcinoma. The cancer can be a brain cancer. In some embodiments, the cancer is a glioblastoma. The cancer can be a renal cancer. In some embodiments, the renal cancer is a clear cell renal carcinoma. In some embodiments, the cancer is a breast cancer. In some embodiments, the cancer is an estrogen receptor negative breast cancer. In some embodiments, the cancer is a head and neck cancer. In some embodiments, the cancer is a melanoma. The cancer can be in an early, intermediate, or late stage. The cancer can be benign or malignant. In some embodiments, the cancer is metastatic.

The method can comprise administering a second anti-neoplastic agent, separately or in combination, wherein the first anti-neoplastic agent enhances the second anti-neoplastic agent. Examples of the second anti-neoplastic agent include, but are not limited to those described above for the anti-neoplastic agents of the compositions of the invention. In some embodiments, the enhancement is sub-additive. In some embodiments, the enhancement is additive. In some embodiments, the enhancement is synergistic. When administering first and second anti-neoplastic agents, a composition of the invention can be administered. However, the two (or more) anti-neoplastic agents need not be administered in the same composition nor do they need to be given simultaneously.

The administration of the first and second anti-neoplastic agents can be simultaneous, sequential or in combination. Accordingly, when both first and second anti-neoplastic agents are administered, they need not be administered simultaneously or in the same way or in the same dose. When administered simultaneously, the first and second anti-neoplastic agents can be administered in the same composition or in different compositions. The first and second anti-neoplastic agents can be administered using the same route of administration or different routes of administration. When administered at different times, the first anti-neoplastic agent can be administered before or after the second anti-neoplastic agent. In some embodiments, administration of the first and second anti-neoplastic agents is alternated. In some embodiments, the respective doses of the first and second anti-neoplastic agents are varied over time. The type of anti-neoplastic agents can be varied over time. When administered at separate times, the separation of the first and second anti-neoplastic agents' administration can be any suitable time period. If administered multiple times, the length of the time period can vary. The separation between administration of the first and second anti-neoplastic agents can be 0 seconds, 1 second, 5 seconds, 10 seconds, 30 seconds, 1 minute, 5 minutes, 10 minutes, 15 minutes, 20 minutes, 30, minutes, 45 minutes, 1 hour, 1.5 hours, 2 hours, 2.5 hours, 3 hours, 4 hours, 5 hours, 7.5 hours, 10 hours, 12 hours, 15 hours, 18 hours, 21 hours, 24 hours, 1.5 days, 2 days, 3 days, 4 days, 5 days, 6 days, 7 days, 10 days, 2 weeks, 3 weeks, 4 weeks, one month, 6 weeks, 8 weeks, two months, three months, four months, five months, six months, 9 months, 1 year, 2 years, 5, years, 10 years, and any intermediate time period of the preceding.

In some embodiments, the therapeutic effect on the cancer cell of administering both the first and second anti-neoplastic agents is less than additive. In some embodiments, the effect is substantially additive. However, the first anti-neoplastic agent preferably potentiates the efficacy of the second anti-neoplastic agent in the therapeutic effect on the cancer cell. In some embodiments, the second anti-neoplastic agent potentiates the efficacy of the first anti-neoplastic agent in the therapeutic effect on the cancer cell.

The first and second anti-neoplastic agents can be administered in synergistic amounts. Accordingly, the administration of both the first and second anti-neoplastic agents can have a synergistic effect on the decrease in cell proliferation whether administered simultaneously, sequentially, or in combination. In some embodiments, the first anti-neoplastic agent increases the efficacy of the second anti-neoplastic agent greater than if the second anti-neoplastic agent were employed alone. In some embodiments, the amount that the second anti-neoplastic agent increases the efficacy of the first anti-neoplastic agent is greater than if the first anti-neoplastic agent were employed alone. The effect of administering both the first and second anti-neoplastic agents can be such that the therapeutic effect on the cancer cell is greater than the additive effect of each being administered alone. When given in synergistic amounts, the first anti-neoplastic agent can enhance the efficacy of the second anti-neoplastic agent even if the amount of first anti-neoplastic agent employed alone, without any second anti-neoplastic agent, would have no substantial therapeutic effect on the cancer cell. For example, even if the first anti-neoplastic agent, e.g., a S1P3 antagonist, does not by itself result in cell death, it can enhance the ability of a second anti-neoplastic agent, e.g., Tamoxifen, to cause cell death. Measurements and calculations of synergism can be performed as described in Teicher, "Assays for In Vitro and In Vivo Synergy," in Methods in Molecular Medicine, vol. 85: Novel Anticancer Drug Protocols, pp. 297-321 (2003) and/or by calculating the combination index (CI) using CalcuSyn software.

The method of treating a cancer cell in a subject with a S1P antagonist provided by the invention can be practiced in addition to radiation treatment and/or surgery, e.g., surgery to remove a tumor or other cancerous growth. In such embodiments, the compounds and compositions of the invention can be administered prior to, concurrent with, and/or subsequent to the radiation and/or surgery. The effect of administration of the S1P antagonist and the radiation and/or surgery can be sub-additive, additive, or synergistic.

A method for identifying a test agent that enhances the efficacy of an anti-neoplastic agent in antagonizing a neoplastic cell is provided by the invention. The method can comprise the following steps. A first sample comprising a neoplastic cell is provided. A second sample comprising a neoplastic cell is provided. The type(s) of neoplastic cell in the first and second samples can be the same. The anti-neoplastic agent is applied to the first and second samples. The test agent is applied to the second sample. The first and second samples are assayed for an anti-neoplastic effect. The test agent is identified as an enhancer or not an enhancer based on the effect measured in the second sample compared to the effect measured in the first sample. The test agent employed is an isolated sphingosine-1-phosphate (S1P) antagonist that selectively binds to an epitope in the extracellular loop between transmembrane domains two and three of sphingosine-1-phosphate receptor subtype 3 (S1P3). In some embodiments, the enhancement is synergistic. Examples of anti-neoplastic results that can be measured include cell stabilization, cell death, growth inhibition, cytoskeletal stabilization, migration inhibition, cell invasion inhibition. Examples of cytoskeletal stabilization comprise a decrease in process retraction, cell surface area reduction, rounding, or any combination thereof. Examples of cell invasion inhibition can include inhibiting the invasion by the cell of tissue or extracellular matrix.

The anti-neoplastic results can be measured using any suitable technique. For example, Cell death can be determined by use of a terminal uridine deoxynucleotidyl transferase dUTP nick end labeling (TUNEL) assay as described by Sgonc, R, et al. (1994) Trends in Genetics 10, 41-42. Materials for the TUNEL assay can be obtained in kit format from Roche Applied Science (Basel, Switzerland). Cell death can also be determined by use of an Annexin V assay as described by Kao, S. Y., et al., (2000) Oncogene 19(18):2240-2248. Materials for the Annexin V assay can be obtained in kit format from Invitrogen Corporation (Carlsbad, Calif.). Cell invasiveness can be assayed by Matrigel invasion assay as described by Melchiori, A., et al., (1992) Cancer Research 52:2353. Materials for the Matrigel invasion assay can be obtained from BD Biosciences (San Jose, Calif.).

In some embodiments, the amount of anti-neoplastic agent applied to the first and second samples is the same, and the effect measured in the second sample is greater than the effect measured in the first sample. In some embodiments, the enhancement of the effect is sub-additive. In some embodiments, the enhancement of the effect is additive. In some embodiments, the enhancement of the effect is synergistic. In some embodiments, the amount of anti-neoplastic agent applied to the second sample is less than the amount of the anti-neoplastic agent applied to the first sample, and the effect measured in the first and the second samples is substantially the same. The test agent can be an isolated sphingosine-1-phosphate (S1P) antagonist that selectively binds to an epitope in the extracellular loop between transmembrane domains two and three of sphingosine-1-phosphate receptor subtype 3 (S1P3).

Any suitable type or types of neoplastic cells can be employed in accordance with the enhancer identification method. For example, the neoplastic cell can comprise a breast cancer cell, a colorectal cancer cell, a cervical cancer cell, an endometrial cancer cell, an ovarian cancer cell, a prostate cancer cell, a lung cancer cell, a glioblastoma cell, and any combination thereof.

Any suitable anti-neoplastic agent can be employed in accordance with the enhancer identification method. Examples of the second anti-neoplastic agent include, but are not limited to those described above for the anti-neoplastic agents of the compositions of the invention.

Methods of preventing and treating systemic inflammation and the pathological coagulation associated with bacterial sepsis, viral hemorrhagic fever, systemic inflammatory response syndromes, and other conditions are provided. For example, a method of preventing or treating disseminated intravascular coagulation in a subject is provided. The method can comprise administering an effective amount of a first anti-coagulation agent comprising an isolated sphingosine-1-phosphate (S1P) antagonist that selectively binds to an epitope in the extracellular loop between transmembrane domains two and three of sphingosine-1-phosphate receptor subtype 3 (S1P3) thereby preventing disseminated intravascular coagulation in the subject. The subject treated in accordance with the invention can have been diagnosed with bacterial sepsis, viral hemorrhagic fever, and other conditions associated with inflammation and coagulation or an increased susceptibility for such a condition.

Uses consistent with the compounds, compositions and methods of the invention are provided. Use of an isolated sphingosine-1-phosphate (S1P) antagonist that selectively binds to an epitope in the extracellular loop between transmembrane domains two and three of sphingosine-1-phosphate receptor subtype 3 (S1P3) to treat a cancer cell in a subject is provided by the invention. The invention also provides use of an isolated sphingosine-1-phosphate (S1P) antagonist that selectively binds to an epitope in the extracellular loop between transmembrane domains two and three of sphingosine-1-phosphate receptor subtype 3 (S1P3) for the manufacture of a medicament to treat cancer. Use of an isolated sphingosine-1-phosphate (S1P) antagonist that selectively binds to an epitope in the extracellular loop between transmembrane domains two and three of sphingosine-1-phosphate receptor subtype 3 (S1P3) for the manufacture of a medicament to prevent disseminated intravascular coagulation as well as associated conditions is provided.

Kits employing compounds and compositions of the invention and that can be employed by the uses and methods of the invention are provided. For example, a kit comprising at least two elements is provided by the invention. First, the kit includes an isolated sphingosine-1-phosphate (S1P) antagonist that selectively binds to an epitope in the extracellular loop between transmembrane domains two and three of sphingosine-1-phosphate receptor subtype 3 (S1P3). Second, the kit includes an anti-neoplastic agent. Examples of the second anti-neoplastic agent include, but are not limited to those described above for the anti-neoplastic agents of the compositions of the invention. For example, the anti-neoplastic agent can be selected from the group consisting of an estrogen receptor binder, an antimetabolite, a taxane, an anthracycline, progestin, a megestrol, an aromatase inhibitor, an epidermal growth factor inhibitor, any prodrug thereof, any salt thereof, and any combination thereof.

A therapeutic agent, which can be a compound and/or a composition, relevant to the invention can comprise a small molecule, a nucleic acid, a protein, an antibody, an aptamer, or any other agent with one or more therapeutic property. For example, the therapeutic agent can be an anti-neoplastic agent.

A nucleic acid or nucleotide sequence includes one or more nucleotides. Exemplary nucleic acids include RNA, DNA, any combination thereof. Nucleic acids can include both naturally occurring as well non-naturally occurring nucleotides, ribonucleic acid nucleotides as well as deoxyribonucleic acid nucleotides. When a nucleic acid is recited it refers generically to DNA and RNA unless the recitation explicitly states that the nucleic acid is a specific one, e.g., DNA or RNA. If a nucleic acid refers to a sequence that contains thymine (t), that does not necessarily indicate that the nucleic acid is DNA; in some embodiments the nucleic acid is RNA and/or DNA. Similarly, if a nucleic acid refers to a sequence that contains uracil (u) that does not necessarily indicate that the nucleic acid is RNA; in some embodiments the nucleic acid is DNA and/or RNA.

The nucleic acid molecules relevant to the invention can readily be obtained in a variety of ways, including, without limitation, chemical synthesis, cDNA or genomic library screening, expression library screening, and/or PCR amplification of cDNA. These methods and others useful for isolating such DNA are set forth, for example, by Sambrook et al., "Molecular Cloning: A Laboratory Manual," Cold Spring Harbor Laboratory Press, Cold Spring Harbor, N.Y. (1989), by Ausubel, et al., eds., "Current Protocols In Molecular Biology," Current Protocols Press (1994), and by Berger and Kimmel, "Methods In Enzymology: Guide To Molecular Cloning Techniques," vol. 152, Academic Press, Inc., San Diego, Calif. (1987).

Chemical synthesis of a nucleic acid molecule can be accomplished using methods well known in the art, such as those set forth by Engels et al., Angew. Chem. Intl. Ed., 28:716-734 (1989). These methods include, inter alia, the phosphotriester, phosphoramidite and H-phosphonate methods of nucleic acid synthesis. Nucleic acids larger than about 100 nucleotides in length can be synthesized as several fragments, each fragment being up to about 100 nucleotides in length. The fragments can then be ligated together to form a full length nucleic acid encoding the polypeptide. One method is polymer-supported synthesis using standard phosphoramidite chemistry.

Alternatively, the nucleic acid can be obtained by screening an appropriate cDNA library prepared from one or more tissue source(s) that express the polypeptide, or a genomic library from any subspecies. The source of the genomic library may be any tissue or tissues from a mammalian or other species believed to harbor a gene encoding a protein relevant to the invention. The library can be screened for the presence of a cDNA/gene using one or more nucleic acid probes (oligonucleotides, cDNA or genomic DNA fragments that possess an acceptable level of homology to the gene or gene homologue cDNA or gene to be cloned) that will hybridize selectively with the gene or gene homologue cDNA(s) or gene(s) that is(are) present in the library. The probes preferably are complementary to or encode a small region of the DNA sequence from the same or a similar species as the species from which the library was prepared. Alternatively, the probes can be degenerate. After hybridization, the blot containing the library is washed at a suitable stringency, depending on several factors such as probe size, expected homology of probe to clone, type of library being screened, number of clones being screened, and the like. Stringent washing solutions can be low in ionic strength and are used at relatively high temperatures.

Another suitable method for obtaining a nucleic acid in accordance with the invention is the polymerase chain reaction (PCR). In this method, poly(A)+ RNA or total RNA is extracted from a tissue that expresses the gene product. cDNA is then prepared from the RNA using the enzyme reverse transcriptase. Two primers typically complementary to two separate regions of the cDNA (oligonucleotides) are then added to the cDNA along with a polymerase such as Taq polymerase, and the polymerase amplifies the cDNA region between the two primers.

The invention provides for the use of isolated, purified or enriched nucleic acid sequences of 15 to 500 nucleotides in length, 15 to 100 nucleotides in length, 15 to 50 nucleotides in length, and 15 to 30 nucleotides in length, which have sequence that corresponds to a portion of one of the nucleotides described herein. The nucleic acid can be at least 17, 20, 22, or 25 nucleotides in length. The nucleic acid sequence can be 30 to 300 nucleotides in length, or 45 to 200 nucleotides in length, or 45 to 100 nucleotides in length.

The nucleic acid can be at least 5, 6, 7, 8, 9, 10, 12, 15, 17, 20, 22, 25, 30, 35, 40, 50, 100, 150, 200, 250, 300, 350, 400, 450, 500, 1000, 10,000, 50,000, 100,000 or more nucleotides in length, or 100,000, 75,00O5 50,000, 10,000, 5,000, 1000, 750, 500, 250, 200, 100, 50, 40, 30, 25, 22, 20, 17, 15, 12, 10, 9, 8, 7, 6, 5, or fewer nucleotides in length. The nucleic acid can have a length in a range from any one of the above lengths to any other of the above lengths including endpoints.

A nucleic acid in accordance with the invention can be 25%, 30%, 35%, 40%, 45%, 50%, 55%, 60%, 65%, 70%, 75%, 80%, 82%, 84%, 86%, 88%, 90%, 91%, 92%, 93%, 94%, 95%, 96%, 97%, 98%, 99%, and 100% identical to reference sequences provided herein. A nucleotide that hybridizes under stringent conditions to a nucleotide described herein can be employed. Unless otherwise specified, percent identities for nucleic acids and amino acid sequences are determined as follows. Percent identity of two nucleic acid sequence or two amino acid sequences is determined using the algorithm of Karlin and Altschul (Proc. Natl. Acad. Sci. USA, 87:2264-2268 (2002), modified as in Karlin and Altschul et al., Proc. Nat. Acad. Sci. USA, 90:5873-5877 (1993). Such an algorithm is incorporated into the NBLAST and XBLAST programs of Altschul et al., J. Mol. Biol. 215: 403-410 (1990). BLAST nucleotide searches are performed with the NBLAST program, score=100, wordlength=1, to obtain nucleotide sequences with a percent identity to a nucleic acid employed in the invention. BLAST protein searches are performed with the XBLAST program, score=50, wordlength=3, to obtain amino acid sequences with a percent identity to a reference polypeptide. To obtain gapped alignments for comparison purposes, Gapped BLAST is utilized as described in Altschul et al., Nucleic Acids Res., 25:3389-3402 (1997). When utilizing BLAST and Gapped BLAST programs, the default parameters of the respective programs (e.g., XBLAST and NBLAST) are used. See <www.ncbi.nih.gov>.

Unless otherwise specified, a nucleic acid and nucleic acid probe can include one or more nucleic acid analogs, labels or other substituents or moieties so long as the base-pairing function is retained. The nucleic acid probe can comprise a detectable label, such as a radioactive or fluorescent label. A variety of other detectable labels are known to those skilled in the art. Unless otherwise specified, where the sequence for a given strand is provided, the invention also includes its complement in addition or in the alternative.

In connection with nucleic acid hybridization, the term "specifically hybridizes" indicates that the probe hybridizes to a sufficiently greater degree to the target sequence than to a non-target sequence, e.g., at a level which allows ready identification of probe/target sequence hybridization under selective hybridization conditions. "Selective hybridization conditions" refer to conditions that allow such differential binding. Similarly, the terms "specifically binds" and "selective binding conditions" refer to such differential binding of any type of probe, and to the conditions that allow such differential binding.

Variables can be adjusted to optimize the specificity of a nucleic acid probe, including changes in salt concentration, temperature, pH and addition of various compounds that affect the differential affinity of GC vs. AT base pairs, such as tetramethyl ammonium chloride. [See Current Protocols in Molecular Biology, Ausubel et al. (Editors), John Wiley & Sons.] Hybridization conditions should be sufficiently stringent such that there is a significant difference in hybridization intensity between alleles, and preferably an essentially binary response, whereby a probe hybridizes to only one of the alleles. Hybridizations can be performed under stringent conditions that allow for specific binding between an oligonucleotide and a target nucleic acid. Stringent conditions are defined as any suitable buffer concentrations and temperatures that allow specific hybridization of the oligonucleotide and any washing conditions that remove non-specific binding of the oligonucleotide. For example, conditions of 5×SSPE (750 mM NaCl, 50 mM Na Phosphate, 5 mM EDTA, pH 7.4) and a temperature of 25-30° C. are suitable for allele-specific probe hybridizations. The washing conditions can range from room temperature to 60° C.

Polypeptides or fragments thereof can be expressed in an expression vector in which a gene or coding segment thereof or related construct thereof is operably linked to a native or other promoter. The promoter can be a eukaryotic promoter for expression in a mammalian cell. The transcription regulation sequences typically include a heterologous promoter and optionally an enhancer that is recognized by the host. The selection of an appropriate promoter, for example trp, lac, phage promoters, glycolytic enzyme promoters and tRNA promoters, depends on the host selected. Commercially available expression vectors can be used. Vectors can include host-recognized replication systems, amplifiable genes, selectable markers, host sequences useful for insertion into the host genome, and the like.

The expression construct can be introduced into a host cell in a number of ways depending upon the particular construction and the target host, for example, fusion, conjugation, transfection, transduction, electroporation, or injection, as described in Sambrook, supra. A wide variety of host cells can be employed for expression of the gene or coding segment thereof or related construct thereof including both prokaryotic and eukaryotic. Suitable host cells include bacteria such as *E. coli*, yeast, filamentous fungi, insect cells, mammalian cells, typically immortalized, e.g., mouse, CHO, human and monkey cell lines and derivatives thereof. In some embodiments, HEK293 cells are used as the host cells. Host cells can be selected to process the translated product to produce an appropriate mature polypeptide. Processing includes glycosylation, ubiquitination, disulfide bond formation, and general post-translational modification.

The protein can be isolated by conventional means of protein biochemistry and purification to obtain a substantially pure product, i.e., 80, 95 or 99% free of cell component contaminants, as described in Jacoby, Methods in Enzymology Volume 104, Academic Press, New York (1984); Scopes, Protein Purification, Principles and Practice, 2nd Edition, Springer-Verlag, New York (1987); and Deutscher (ed), Guide to Protein Purification, Methods in Enzymology, Vol. 182 (1990). If the protein is secreted, it can be isolated from the supernatant in which the host cell is grown. If not secreted, the protein can be isolated from a lysate of the host cells. In the case of antibodies, the antibody can be purified from serum, ascites fluid, or cell supernatant by several methods including affinity purification or protein A/G purification. Affinity purification can be performed using an EpiMax purification kit per manufacturer's protocol (Epitomics, Inc., Burlingame, Calif.). Protein A/G purification can be performed using protein A/G chromatography columns, or protein A/G-conjugated resin per manufacturer's protocol (Thermo Scientific, Rockford, Ill.).

In addition to substantially full-length polypeptides expressed by genes or coding segments thereof, the invention includes use of biologically active fragments of the polypeptides, or analogs thereof, including organic molecules that simulate the interactions of the peptides. Biologically active fragments include any portion of the full-length polypeptide that confers a biological function on the expressed product, including ligand binding and antibody binding. Ligand binding includes binding by nucleic acids, proteins or polypeptides, small biologically active molecules or large cellular structures. In some embodiments, the polypeptide is at least 5, 6, 7, 8, 9, 10, 12, 15, 17, 20, 22, 25, 30, 35, 40, 50, 100, 150, 200, 250, 300, 350, 400, 450, 500, 1000, 10,000, 50,000, 100,000 or more amino acids in length, or 100,000, 75,000, 50,000, 10,000, 5,000, 1000, 750, 500, 250, 200, 100, 50, 40, 30, 25, 22, 20, 17, 15, 12, 10, 9, 8, 7, 6, 5, or fewer amino acids in length. A polypeptide can have a length in a range from any one of the above lengths to any other of the above lengths including endpoints. A polypeptide in accordance with the invention can be 25%, 30%, 35%, 40%, 45%, 50%, 55%, 60%, 65%, 70%, 75%, 80%, 82%, 84%, 86%, 88%, 90%, 91%, 92%, 93%, 94%, 95%, 96%, 97%, 98%, 99%, and 100% identical to reference sequence provided herein.

Antibodies specific for an epitope in the extracellular loop between transmembrane domains two and three of sphingosine-1-phosphate receptor subtype 3 (S1P3) and polypeptides comprising antigen binding fragments thereof are provided as well as methods, uses, compositions, and kits employing the same. A method of forming an antibody specific to a human epitope in the extracellular loop between transmembrane domains two and three of sphingosine-1-phosphate receptor subtype 3 (S1P3) or a polypeptide a fragment thereof is provided. Such a method can comprise providing a nucleic acid encoding a S1P3 polypeptide or a polypeptide comprising an immunologically specific epitope thereof; expressing a S1P3 polypeptide comprising a S1P3 amino acid sequence or a polypeptide comprising an immunologically specific epitope thereof from the isolated nucleic acid; and generating an antibody specific to the polypeptide obtained in step or a polypeptide comprising an antigen binding fragment thereof. An antibody or polypeptide comprising an antigen binding fragment thereof produced by the aforementioned method is provided. An isolated antibody or isolated polypeptide comprising an antigen binding fragment thereof that specifically binds a human epitope in the extracellular loop between transmembrane domains two and three of S1P3 comprising a S1P3 amino acid sequence is provided. Such an antibody can be generated using any acceptable method(s) known in the art. The antibodies as well as kits, methods, and other aspect of the invention employing antibodies can comprise one or more of the following: a polyclonal antibody, a monoclonal antibody, a chimeric antibody, a single-chain antibody, a monovalent antibody, a diabody, and a humanized antibody.

Naturally occurring antibody structural units typically comprise a tetramer. Each such tetramer typically is composed of two identical pairs of polypeptide chains, each pair having one full-length "light" (in certain embodiments, about 25 kDa) and one full-length "heavy" chain (in certain embodiments, about 50-70 kDa). The amino-terminal portion of each chain typically includes a variable region of about 100 to 110 or more amino acids that typically is responsible for antigen recognition. The carboxy-terminal portion of each chain typically defines a constant region that may be responsible for effector function. Human light chains are typically classified as kappa and lambda light chains. Heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. In light and heavy chains, the variable and constant regions can be joined by a "J" region of about 12 or more amino acids, with the heavy chain also including a "D" region of about 10 more amino acids. See, e.g., Fundamental Immunology Ch. 7 (Paul, W., ed., 2nd ed. Raven Press, N.Y. (1989)) (incorporated by reference in its entirety for all purposes). The variable regions of each light/heavy chain pair typically form the antigen binding site.

The variable regions typically exhibit the same general structure of relatively conserved framework regions (FR) joined by three hyper variable regions, also called complementarity determining regions or CDRs. The CDRs from the two chains of each pair typically are aligned by the framework regions, which may enable binding to a specific epitope. From N-terminal to C-terminal, both light and heavy chain variable regions typically comprise the domains FR1, CDR1, FR2, CDR2, FR3, CDR3 and FR4. The assignment of amino acids to each domain is typically in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987); Chothia et al. Nature 342:878-883 (1989).

"Antibody fragments" comprise a portion of an intact antibody, such as the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 [1995]); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen-combining sites and is still capable of cross-linking antigen. "Fv" is an antibody fragment which contains a complete antigen-recognition and -binding site. This region consists of a dimer of one heavy- and one light-chain variable domain in tight, non-covalent association. A single variable domain (or half of an Fv comprising only three CDRs specific for an antigen) can recognize and bind antigen. "Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

Antibodies can be used as probes, therapeutic treatments and other uses. Polyclonal and/or monoclonal antibodies and antibody fragments capable of binding to a portion of the gene product relevant for identifying a given target are provided. Antibodies can be made by injecting mice, rabbits, goats, or other animals with the translated product or synthetic peptide fragments thereof. Monoclonal antibodies are screened as are described, for example, in Harlow & Lane, Antibodies, A Laboratory Manual, Cold Spring Harbor Press, New York (1988); Goding, Monoclonal antibodies, Principles and Practice (2d ed.) Academic Press, New York (1986). Monoclonal antibodies are tested for specific immunoreactivity with a translated product and lack of immunoreactivity to the corresponding prototypical gene product. These antibodies are useful in diagnostic assays or as an active ingredient in a pharmaceutical composition.

The antibodies of the present invention can be coupled directly or indirectly to a detectable marker by techniques well known in the art. In some embodiments, the antibody used is a monoclonal antibody. A detectable marker is an agent detectable, for example, by spectroscopic, photochemical, biochemical, immunochemical, or chemical means. Useful detectable markers include, but are not limited to, fluorescent dyes, chemiluminescent compounds, radioisotopes, electron-dense reagents, enzymes, colored particles, biotin, or dioxigenin. A detectable marker often generates a measurable signal, such as radioactivity, fluorescent light, color, or enzyme activity. Antibodies conjugated to detectable agents may be used for diagnostic or therapeutic purposes. Examples of detectable agents include various enzymes, prosthetic groups, fluorescent materials, luminescent materials, bioluminescent materials, radioactive materials, positron emitting metals using various positron emission tomographies, and nonradioactive paramagnetic metal ions. The detectable substance can be coupled or conjugated either directly to the antibody or indirectly, through an intermediate such as, for example, a linker known in the art, using techniques known in the art. See, for example, U.S. Pat. No. 4,741,900, describing the conjugation of metal ions to antibodies for diagnostic use. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferin, and aequorin.

Polyclonal or monoclonal therapeutic antibodies useful in practicing this invention can be prepared in laboratory animals or by recombinant DNA techniques using the following methods. Polyclonal antibodies are raised in animals by multiple subcutaneous (sc) or intraperitoneal (ip) injections of the gene product molecule or fragment thereof in combination with an adjuvant such as Freund's adjuvant (complete or incomplete). To enhance immunogenicity, it may be useful to first conjugate the gene product molecule or a fragment containing the target amino acid sequence to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOCl, etc. Alternatively, immunogenic conjugates can be produced recombinantly as fusion proteins.

Animals can be immunized against the immunogenic conjugates or derivatives (such as a fragment containing the target amino acid sequence) by combining about 1 mg or about 1 microgram of conjugate (for rabbits or mice, respectively) with about 3 volumes of Freund's complete adjuvant and injecting the solution intradermally at multiple sites. Approximately 7 to 14 days later, animals are bled and the serum is assayed for antibody titer. Animals are boosted with antigen repeatedly until the titer plateaus. The animal can be boosted with the same molecule or fragment thereof as was used for the initial immunization, but conjugated to a different protein and/or through a different cross-linking agent. In addition, aggregating agents such as alum are used in the injections to enhance the immune response.

The anti-S1P3 antibodies of the invention can be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

Monoclonal antibodies can be prepared by recovering spleen cells from immunized animals and immortalizing the cells in conventional fashion, e.g., by fusion with myeloma cells. The clones are then screened for those expressing the desired antibody. The monoclonal antibody preferably does not cross-react with other gene products. After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal. The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody. Preparation of Antibodies Using Recombinant DNA Methods Such as the Phagemid Display method, can be accomplished using commercially available kits, as for example, the Recombinant Phagemid Antibody System available from Pharmacia (Uppsala, Sweden), or the SurfZAP™ phage display system (Stratagene Inc., La Jolla, Calif.).

Also included in the present invention are hybridoma cell lines, transformed B cell lines, and host cells that produce the monoclonal antibodies of the present invention; the progeny or derivatives of these hybridomas, transformed B cell lines, and host cells; and equivalent or similar hybridomas, transformed B cell lines, and host cells. Examples of hybridoma cells lines include without limitation EDDbeta7H9 and EDDbeta7F6. Hybridoma EDDbeta7H9 produces the monoclonal antibody Mab7H9. Hybridoma EDDbeta7F6 produces monoclonal antibody Mab7F6.

With regard to monoclonal antibody 7H9 produced by hybridoma cell line referred to as EDDbeta 7H9, hybridoma B-cell/myeloma, *Mus musculus*, MAS 1130 clone 7H9F11, was deposited at the American Type Culture Collection (10801 University Blvd., Manassas, Va. 20110-2209 USA (ATCC) on Apr. 24, 2009, and bears accession number PTA-9973.

| Hybridoma/Antibody Designation | ATTC No. | Deposit Date |
|---|---|---|
| EDDbeta7H9 | PTA-9973 | April 24, 2009 |
| EDDbeta7F6 | | |

This deposit is made under the provisions of the Budapest Treaty on the International Recognition of the Deposit of Microorganisms for the Purpose of Patent Procedure and the Regulations thereunder (Budapest Treaty). This assures maintenance of a viable culture for 30 years from the date of deposit. The cell line will be made available by ATCC under the terms of the Budapest Treaty, and subject to an agreement between the assignee and ATCC, which assures (a) that access to the culture will be available during pendency of the patent application to one determined by the Commissioner to be entitled thereto under 37 CFR §1.14 and 35 USC §122, and (b) that all restrictions on the availability to the public of the culture so deposited will be irrevocably removed upon the granting of the patent.

The assignee of the present application agrees that if the culture on deposit should die or be lost or destroyed when cultivated under suitable conditions, it will be promptly replaced on notification with a viable specimen of the same culture. Availability of the deposited cell line is not to be construed as a license to practice the invention in contravention of the rights granted under the authority of any government in accordance with its patent laws.

Monoclonal antibodies of the present invention include monoclonal antibodies having the same heavy chain as Mab7H9 or Mab7F6. Monoclonal antibodies of the present invention include monoclonal antibodies having the same light chain as Mab7H9 or Mab7F6. Monoclonal antibodies of the present invention include monoclonal antibodies having the same heavy chain and the same light chain as Mab7H9 or Mab7F6. Such monoclonal antibodies can bind to S1P3. Such monoclonal antibodies can inhibit the binding of Mab7H9 or Mab7F6 to S1P3. Such monoclonal antibodies can bind to the same epitope of S1P3 that is recognized by Mab7H9 or Mab7F6. The present invention also includes such monoclonal antibodies containing one, two, three, four, five, six, or more amino acid substitutions in the heavy and/or the light chains that do not substantially affect the ability of the antibody to bind S1P3.

Monoclonal antibodies of the present invention include monoclonal antibodies having the same $V_H$ domain as Mab7H9 or Mab7F6. Monoclonal antibodies of the present invention include monoclonal antibodies having the same $V_L$ domain as Mab7H9 or Mab7F6. Monoclonal antibodies of the present invention include monoclonal antibodies having the same $V_H$ domain and the same $V_L$ domain as Mab7H9 or Mab7F6. Such monoclonal antibodies can bind to S1P3. Such monoclonal antibodies can inhibit the binding of Mab7H9 or Mab7F6 to S1P3. Such monoclonal antibodies can bind to the same epitope of S1P3 that is recognized by Mab7H9 or Mab7F6. The present invention also includes such monoclonal antibodies containing one, two, three, four, five, six, or more amino acid substitutions in the $V_H$ domain and/or $V_L$ domain that do not substantially affect the ability of the antibody to bind S1P3.

Monoclonal antibodies of the present invention include monoclonal antibodies having at least one CDR region of the $V_H$ domain of Mab7H9 or Mab7F6; at least two CDR regions of the $V_H$ domain of Mab7H9 or Mab7F6; or at least three CDR regions of the $V_H$ domain of Mab7H9 or Mab7F6; and/or at least one CDR region of the $V_L$ domain of Mab7H9 or Mab7F6; at least two CDR regions of the $V_L$ domain of Mab7H9 or Mab7F6; or at least three CDR regions of the $V_L$ domain of Mab7H9 or Mab7F6. Such monoclonal antibodies can bind to S1P3. Such monoclonal antibodies can inhibit the binding of Mab7H9 or Mab7F6 to S1P3. Such monoclonal antibodies can bind to the same epitope of S1P3 that is recognized by Mab7H9 or Mab7F6. The monoclonal antibodies of the present invention further include monoclonal antibodies containing one, two, three, four, five, six, or more amino acid substitutions in one or more CDR regions which do not substantially affect the ability of the antibody to bind S1P3.

Monoclonal antibodies of the present invention include monoclonal antibodies having an amino acid sequence at least about 70%, at least about 80%, at least about 85%, at least about 90%, at least about 95%, at least about 96%, at least about 97%, at least about 98%, or at least about 99% identical to an amino acid sequence of at least one CDR region of a $V_H$ domain of the antibody expressed by hybridoma cell line EDDbeta7H9 or EDDbeta7F6; at least two CDR regions of a $V_H$ domain of the antibody expressed by hybridoma cell line EDDbeta7H9 or EDDbeta7F6; or at least three CDR regions of a $V_H$ domain of the antibody expressed by hybridoma cell line EDDbeta7H9 or EDDbeta7F6. Such a monoclonal antibody can bind to S1P3. Such monoclonal antibodies can inhibit the binding of Mab7H9 or Mab7F6 to S1P3. Such monoclonal antibodies can bind to the same epitope of S1P3 that is recognized by Mab7H9 or Mab7F6.

Monoclonal antibodies of the present invention include antibodies having an amino acid sequence at least about 70%, at least about 80%, at least about 85%, at least about 90%, at least about 95%, at least about 96%, at least about 97%, at least about 98%, or at least about 99% identical to an amino acid sequence of at least one CDR region of a $V_L$ domain of the antibody expressed by hybridoma cell line EDDbeta7H9 or EDDbeta7F6; at least two CDR regions of a $V_L$ domain of the antibody expressed by hybridoma cell line EDDbeta7H9 or EDDbeta7F6; or at least three CDR regions of a $V_L$ domain of the antibody expressed by hybridoma cell line EDDbeta7H9 or EDDbeta7F6. Such an antibody may bind to S1P3. Such monoclonal antibodies can inhibit the binding of Mab7H9 or Mab7F6 to S1P3. Such monoclonal antibodies can bind to the same epitope of S1P3 that is recognized by Mab7H9 or Mab7F6.

In some embodiments, the antibodies are diabodies. The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains can be forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

In some embodiments, the antibodies are monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking. In vitro methods are also suitable for preparing monovalent antibodies. Digestion of antibodies to produce fragments thereof, particularly, Fab fragments, can be accomplished using routine techniques known in the art.

In some embodiments, the antibodies are bispecific. Bispecific antibodies that specifically bind to one protein and that specifically bind to other antigens relevant to pathology and/or treatment are produced, isolated, and tested using standard procedures that have been described in the literature. [See, e.g., Pluckthun & Pack, Immunotechnology, 3:83-105 (1997); Carter, et al., J. Hematotherapy, 4:463-470 (1995); Renner & Pfreundschuh, Immunological Reviews, 1995, No. 145, pp. 179-209; Pfreundschuh U.S. Pat. No. 5,643,759; Segal, et al., J. Hematotherapy, 4:377-382 (1995); Segal, et al., Immunobiology, 185:390-402 (1992); and Bolhuis, et al., Cancer Immunol. Immunother., 34: 1-8 (1991)].

In some embodiments, the antibodies are humanized or partially humanized. Non-human antibodies can be humanized using any applicable method known in the art. A humanized antibody can be produced using a transgenic animal whose immune system has been partly or fully humanized. Any antibody or fragment thereof of the invention can be partially or fully humanized. Chimeric antibodies can be produced using any known technique in the art. See, e.g., U.S. Pat. Nos. 5,169,939; 5,750,078; 6,020,153; 6,420,113; 6,423, 511; 6,632,927; and 6,800,738.

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate). Cytotoxic agents can be anti-neoplastic agents and vice versa. That is, an agent used as a cytotoxic agent can be used as an anti-neoplastic agent and vice versa. Chemotherapeutic agents can be used in the generation of immunoconjugates, e.g., methotrexate, adriamycin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Auristatin, maytansinoid and calicheamicin are examples of toxins that can be employed. Enzymatically active toxins and fragments thereof that can be used include, for example, diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. Any appropriate radionucleotides or radioactive agent known in the art or are otherwise available can be used to produce radioconjugated antibodies.

Conjugates of the antibody and cytotoxic agent can be made using a variety of bifunctional protein-coupling agents such as N-succinimidyl-3-(2-pyridyldithiol)propionate (SPDP); iminothiolane (IT); bifunctional derivatives of imidoesters (such as dimethyl adipimidate HCL); active esters (such as disuccinimidyl suberate); aldehydes (such as glutareldehyde); bis-azido compounds (such as bis(p-azidobenzoyl) hexanediamine); bis-diazonium derivatives (such as bis-(p-diazoniumbenzoyl)-ethylenediamine); diisocyanates (such as tolyene 2,6-diisocyanate); bis-active fluorine compounds (such as 1,5-difluoro-2,4-dinitrobenzene); maleimidocaproyl (MC); valine-citrulline, dipeptide site in protease cleavable linker (VC); 2-amino-5-ureido pentanoic acid PAB=p-aminobenzylcarbamoyl ("self immolative" portion of linker) (Citrulene); N-methyl-valine citrulline where the linker peptide bond has been modified to prevent its cleavage by cathepsin B (Me); maleimidocaproyl-polyethylene glycol, attached to antibody cysteines (MC(PEG)6-OH); N-Succinimidyl 4-(2-pyridylthio)pentanoate (SPP); and N-Succinimidyl 4-(N-maleimidomethyl)cyclohexane-1 carboxylate (SMCC). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. In some embodiments, the antibody is conjugated to a "receptor" (such streptavidin) for utilization in tumor pretargeting wherein the antibody-receptor conjugate is administered to the subject, followed by removal of unbound conjugate from the circulation using a clearing agent and then administration of a "ligand" (e.g., avidin) that is conjugated to a cytotoxic agent (e.g., a radionucleotide).

The antibodies disclosed herein can be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA 77: 4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction. A chemotherapeutic agent (such as Doxorubicin) is optionally contained within the liposome. See Gabizon et al., J. National Cancer Inst., 81 (19): 1484 (1989).

Aptamers can be selected and produced using any suitable technique or protocol. For example, oligonucleotide libraries with variable regions ranging from 18 to 50 nucleotides in length can be used as templates for run-off transcription reactions to generate random pools of RNA aptamers. The resulting pools are extremely diverse containing a theoretical maximum of $1.27 \times 10^{30}$ unique species with the largest library. This aptamer pool is then exposed to unconjugated matrix to remove non-specific interacting species. The remaining pool is then incubated with an immobilized target. The majority of aptamer species in this pool having low affinity for the target will be washed away leaving a smaller, more specific pool bound to the matrix. This pool is then eluted, precipitated, reverse transcribed, and used as a template for run-off transcription. After five rounds of selection, aliquots are removed that are cloned and sequenced. Selection continues until similar sequences are reproducibly recovered.

Aptamer production can be performed using a bead-based selection system. In this process, a library of beads is generated in which each bead is coated with a population of aptamers with identical sequences composed of natural and modified nucleotides. This bead library, containing >100,000,000 unique sequences, is incubated with a peptide that corresponds to the extracellular loop between transmembrane domains 2 and 3 of S1P3 that is conjugated with a tag such as a fluorescent dye. In some embodiments, the peptide employed comprises the amino acid sequence KKTFSL-SPTVWFLREG (SEQ ID NO: 1). After washing, beads that demonstrate the highest binding affinity are isolated and aptamer sequences are determined for subsequent synthesis.

A therapeutic agent in accordance with the invention can be formulated in any pharmaceutically acceptable manner. In some embodiments, the therapeutic agent is prepared in a depot form to allow for release into the body to which it is administered is controlled with respect to time and location within the body (see, for example, U.S. Pat. No. 4,450,150). Depot forms of therapeutic agents can be, for example, an implantable composition comprising the therapeutic agent and a porous or non-porous material, such as a polymer, wherein the therapeutic agent is encapsulated by or diffused throughout the material and/or degradation of the non-porous material. The depot is then implanted into the desired location within the body and the therapeutic agent is released from the implant at a predetermined rate.

The therapeutic agent that is used in the invention can be formed as a composition, such as a pharmaceutical composition comprising a carrier and a therapeutic compound. Pharmaceutical compositions containing the therapeutic agent can comprise more than one therapeutic agent. The pharmaceutical composition can alternatively comprise a therapeutic agent in combination with other pharmaceutically active agents or drugs, such as chemotherapeutic agents, for example, a cancer drug.

The carrier can be any suitable carrier. Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. In addition to the following described pharmaceutical composition, the therapeutic compounds of the present inventive methods can be formulated as inclusion complexes, such as cyclodextrin inclusion complexes, or liposomes.

The pharmaceutically acceptable carriers described herein, for example, vehicles, adjuvants, excipients, and diluents; are well-known to those skilled in the art and are readily available to the public. The pharmaceutically acceptable carrier can be chemically inert to the active agent(s) and one which has no detrimental side effects or toxicity under the conditions of use. The choice of carrier can be determined in part by the particular therapeutic agent, as well as by the particular method used to administer the therapeutic compound. There are a variety of suitable formulations of the pharmaceutical composition of the invention. The following formulations for oral, aerosol, parenteral, subcutaneous, transdermal, transmucosal, intestinal, intramedullary injections, direct intraventricular, intravenous, intranasal, intraocular, intramuscular, intraarterial, intrathecal, intraperitoneal, rectal, and vaginal administration are exemplary and are in no way limiting. More than one route can be used to administer the therapeutic agent, and in some instances, a particular route can provide a more immediate and more effective response than another route. Depending on the specific disorder being treated, such agents can be formulated and administered systemically or locally. Techniques for formulation and administration may be found in Remington's Pharmaceutical Sciences, 18th ed., Mack Publishing Co., Easton, Pa. (1990).

Formulations suitable for oral administration can include (a) liquid solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or soft shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inhibitor in a flavor, usually sucrose and acacia or tragacanth, as well as pastilles comprising the inhibitor in an inert base, such as gelatin and glycerin, or sucrose and acacia, emulsions, gels, and the like containing, in addition to, such excipients as are known in the art.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The therapeutic agent, alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non pressured preparations, such as in a nebulizer or an atomizer. Such spray formulations also may be used to spray mucosa. Topical formulations are well known to those of skill in the art. Such formulations are particularly suitable in the context of the invention for application to the skin.

Injectable formulations are in accordance with the invention. The parameters for effective pharmaceutical carriers for injectable compositions are well-known to those of ordinary skill in the art [see, e.g., Pharmaceutics and Pharmacy Practice, J.B. Lippincott Company, Philadelphia, Pa., Banker and Chalmers, eds., pages 238250 (1982), and ASHP Handbook on Injectable Drugs, Toissel, 4th ed., pages 622 630 (1986)]. For injection, the agents of the invention can be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Formulations suitable for parenteral administration include aqueous and non aqueous, isotonic sterile injection solutions, which can contain anti oxidants, buffers, bacteriostats, and solutes that render the formulation isotonic with the blood of the intended recipient, and aqueous and non aqueous sterile suspensions that can include suspending agents, solubilizers, thickening agents, stabilizers, and preservatives. The therapeutic agent can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, poly(ethyleneglycol) 400, glycerol, dimethylsulfoxide, ketals such as 2,2-dimethyl-1,3-dioxolane-4-methanol, ethers, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the drug in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight.

Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The therapeutic agent can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The exact formulation, route of administration and dosage can be chosen by the individual physician in view of the patient's condition. [See, e.g., Fingl et. al., in The Pharmacological Basis of Therapeutics, 1975, Ch. 1 p. I]. The attending physician can determine when to terminate, interrupt, or adjust administration due to toxicity, or to organ dysfunctions. Conversely, the attending physician can also adjust treatment to higher levels if the clinical response were not adequate, precluding toxicity. The magnitude of an administrated dose in the management of disorder of interest will vary with the severity of the disorder to be treated and the route of administration. The severity of the disorder can, for example, be evaluated, in part, by standard prognostic evaluation methods. The dose and perhaps dose frequency, can vary according to the age, body weight, and response of the individual patient. A program comparable to that discussed above can be used in veterinary medicine.

Use of pharmaceutically acceptable carriers to formulate the compounds herein disclosed for the practice of the invention into dosages suitable for systemic administration is within the scope of the invention. With proper choice of carrier and suitable manufacturing practice, the compositions relevant to the invention, in particular, those formulated as solutions, can be administered parenterally, such as by intravenous injection. The compounds can be formulated readily using pharmaceutically acceptable carriers well known in the art into dosages suitable for oral administration. Such carriers enable the compounds relevant to the invention to be formulated as tablets, pills, capsules, liquids, gels, syrups, slurries, tablets, dragees, solutions, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. Molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly. Materials and methods described for one aspect of the invention can also be employed in other aspects of the invention. For example, a material such a nucleic acid or antibody described for use in screening assays can also be employed as therapeutic agents and vice versa.

The following examples further illustrate the invention but, of course, should not be construed as in any way limiting its scope.

EXAMPLE 1

This example demonstrates an example of an isolated sphingosine-1-phosphate (S1P) antagonist that selectively binds to an epitope in the extracellular loop between transmembrane domains two and three of sphingosine-1-phosphate receptor subtype 3 (S1P3) in accordance with the invention. Polyclonal antiserum that specifically recognizes S1P3 is produced.

Rabbits are immunized with a synthetically-generated peptide of the sequence KKTFSLSPTVWFLREG (SEQ ID NO: 1). This sequence is found in the extracellular loop of S1P3 between transmembrane domains 2 and 3. This primary sequence is unique and shares little similarity to the same motif in the other four known S1P-specific receptors.

HEK293 cells are transiently transfected with constructs that overexpress the indicated receptor. A C-terminal epitope tag (V5) is used to verify transfection, expression, and appropriate plasma membrane localization. Cells are fixed with 4% paraformaldehyde, permeabilized with 0.1% Triton X-100, blocked with 2.5% bovine serum albumin, and exposed to the S1P3 antiserum at a concentration of 1:1,000. Bound antibody is detected with a Cy3-conjugated ant-rabbit antibody and visualized with fluorescence microscopy. Serum from the immunized rabbits specifically binds to HEK293 cells that overexpress S1P3, but not to HEK293 cells that overexpress S1P1 or S1P2.

EXAMPLE 2

This example demonstrates that S1P3 is expressed in human breast tumor cell lines, cell lines that can be employed in the examples that follow and in the methods of the invention generally.

Quantitative real-time RT-PCR is performed to determine expression of the five known high affinity S1P-specific receptors (S1P1-S1P5) in two breast cancer cell lines (MCF-7 and MDA-MB-231). Copy number is determined by standardization to samples of known concentrations, and represented relative to the house-keeping gene, cyclophilin A. Total RNA is isolated from cells using TRIZOL (Life Technologies) according to the manufacturer's protocol. After DNAse treatment (RNAse-free DNAse, Fermentas), RNA samples are reverse-transcribed into cDNA using oligo (dT) 12-18 (SEQ ID NO: 2) and Super Script™ II Reverse transcriptase (Invitrogen), cDNA is amplified by Taq DNA Polymerase in 10×PCR Buffer using the manufacturer's protocol. For quantification by real time RT-PCR, targets are amplified with iQ sybr green supermix (Bio-Rad cat #170-8880) on a Bio-Rad iCycler. Copy number is determined by comparison to standard curves using plasmid templates containing reference sequences at known concentrations.

In both lines, S1P3 is the most abundant species. S1P4 and S1P5 are not detected in either sample.

TABLE 1

| mRNA Copy #/Copy Cyclophilin A (X10-4) | | |
| --- | --- | --- |
| Receptor Subtype | MCF-7 | MDA-MB-231 |
| S1P1 | 0 | 0.258 |
| S1P2 | 0.110 | 0.0721 |
| S1P3 | 1.56 | 0.403 |
| S1P4 | 0 | 0 |
| S1P5 | 0 | 0 |

In addition, cDNA prepared from an invasive ductal carcinoma from a 54 year-old female is amplified by non-quantitative RT-PCR with S1P3-specific primers that span an intron splice site. A band of the predicted size is obtained, thus verifying the expression of S1P3 in a clinically-derived breast tumor.

EXAMPLE 3

This example demonstrates the ability of an antagonist of the invention to have an anti-neoplastic effect such as the inhibition of cell proliferation and/or mobility. The effect measured is the ability of S1P to induce cytoskeletal rearrangement in breast cancer cells (BCCs).

The experiments can be first performed in the absence of the antagonist to demonstrate that S1P induces cytoskeletal rearrangement in BCCs. MDA-MB-231 breast cancer cells are cultured on collagen-coated coverslips in the presence of 10% FBS using standard techniques. Because S1P is present at high concentrations in serum, BCCs are "serum-starved" in Dulbecco's modified Eagle medium (DMEM) for 12 hours prior to experimental manipulation. S1P is solubilized with bovine serum albumin (BSA) carrier and administered at a final concentration of 1 nM to 1 µM. Coverslips are collected at representative time points such as 10 minutes, 1 hr., 2 hrs., 4 hrs., and 6 hrs., fixed with 4% paraformaldehyde, and stained with rhodamine-conjugated phalloidin to label cytoskeletal actin.

Upon application of 1 µM S1P to breast cancer cells in culture, marked cytoskeletal rearrangement is apparent in the majority of the cells (>90%) within 10 minutes. There is a near complete collapse of the cytoplasmic extensions and cell rounding. This morphological change persists for at least one hour. By two hours after administration, the cells begin to show signs of recovery with cell spreading and membrane ruffling. At four hours, most cells begin re-extending processes, and return to normal morphology by six hours. S1P is highly potent in its ability to elicit cytoskeletal rearrangement in BCCs by inducing cell rounding at low concentrations. There are minor cell shape changes at 1 nM and dramatic cell rounding at 10 nM. This is significant in that the concentration of S1P in human serum is ~100 nM, which is far greater than that needed to be functionally active.

The cell rounding experiment can be performed using an antagonist of S1P that binds to S1P3. For example, the antiserum described in Example 1 can be employed. Serum-starved MDA-MB-231 cells are incubated with preimmune serum or S1P3-reactive antiserum for 15 minutes prior to a 30-minute exposure to 10 nM S1P, then evaluated for response both in % cells responding and average cell area.

MDA-MB-231 cells are grown under standard culture conditions and serum starved for 24 hours prior to experimental manipulation. S1P3 antiserum or pre-immune serum obtained from the same rabbit is added to the media at a final concentration of 1:10,000 as indicated. 15 minutes later, S1P is added to the media to a final concentration of 10 nM. 30 minutes after S1P administration, cells are fixed with 4% paraformaldehyde, stained with rhodamine-conjugated phalloidin, and visualized with fluorescence microscopy. Rounded cells are counted by an experimenter blinded to the identity of the sample. Cell area is determined by quantification with imageJ software. Results are shown in Tables 2 and 3.

TABLE 2

| % Rounded Cells Following S1P Treatment. | | | |
| --- | --- | --- | --- |
|  | no serum | pre-immune | anti-serum |
| no S1P | 40% | 36% | 43% |
| 10 nM S1P | 64% | 72% | 47% |

TABLE 3

| Average Cell Area Following S1P Treatment ($\mu m^2$) | | | |
| --- | --- | --- | --- |
|  | no serum | pre-immune | anti-serum |
| no S1P | 1555.082358 | 1609.167689 | 1433.854 |
| 10 nM S1P | 960.3760466 | 874.4910888 | 1611.684 |

The concentration of serum used (1:10,000) itself is not sufficient to induce cell rounding. While preimmune-treated cells respond to S1P identically to untreated controls, antiserum-treated cells fail to respond and maintained the shape of cells not exposed to S1P. This result is consistent with the model that the antiserum, and antagonists according to the invention generally, can block the effects of S1P on cancer cells.

EXAMPLE 4

This example demonstrates that an S1P antagonist in accordance with the invention can inhibit the induction by S1P of cancer cell proliferation.

The experiment can first be performed in the absence of the antagonist. The effect of S1P on cell proliferation is determined by measuring bromodeoxyuridine (BrdU) incorporation. In this assay, cells are treated with S1P or vehicle control (0.1% fatty acid-free BSA) for 30 minutes before being exposed to a 30-minute BrdU pulse. Cells are then fixed with ethanol, labeled with a biotinylated α-BrdU antibody, incubated with streptavidin-peroxidase, developed with DAB, and counter-stained with hematoxylin. Nuclei of cells in S-phase during the 30-minute pulse are labeled brown, while non-proliferative cells show the blue hematoxylin stain. The results are shown in Table 4.

TABLE 4

| Dose-Dependent Increase in Mitosis in Two Breast Cancer Cell Lines (MCF-7 and MDA-MB-231) by S1P as Determined By BrdU Incorporation | | | | |
| --- | --- | --- | --- | --- |
| [S1P] | 0 | 10 nM | 100 nM | 1 µM |
| MCF-7 | 34% | 49% | 45% | 61% |
| MDA-MB-231 | 74% | 71% | 84% | 88% |

The presence of S1P causes a dose-dependent increase in mitosis in two breast cancer cell lines (MCF-7 and MDA-MB-231) as determined by BrdU incorporation. When the experiment is performed in the presence of one or more S1P3 antagonist of the invention that increase in mitosis is diminished or eliminated.

Determination of the effect of S1P3 blocking antibodies on the proliferation of cancer cells can be performed as follows. Cancer cells, including MCF-7 and MDA-MB-231 cells, are grown under standard conditions as adherent cell culture with Dulbecco's modified Eagle medium (DMEM) supplemented with 10% fetal bovine serum (FBS), glutamine, and penicillin/streptavidin. Cells are "serum-starved" for at least 12 hours prior to experimental manipulation by culturing in DMEM only. Cultures are then pre-treated with blocking anti-serum, or purified blocking antibodies. Control cultures are treated with pre-immune serum or with non-specific control antibodies. Cells are then stimulated with S1P at varying concentrations (including 1 nM, 10 nM, 100 nM, 1 μM, 10 μM, or any intermediate concentration) or with FBS at varying concentrations (for example 1%, 5%, or 10%). Control cultures without stimulation are run in parallel.

Following a period of stimulation (usually 0.25, 0.5, 0.75, 1, 1.5, 2, 3, 4, or some intermediate period) cells are pulsed with bromodeoxyuridine (BrdU) obtained from Invitrogen Corporation (Carlsbad, Calif.). The pulse period is usually 5, 10, 15, 30, 60, 90, or 120 minutes. Cells are then fixed with 70% ethanol for at least 20 minutes and labeled for the presence of incorporated BrdU with a commercial BrdU labeling kit obtained from Invitrogen Corporation (Carlsbad, Calif.). Alternatively, following fixation, cells are treated with HCl to gently denature the DNA, blocked with a solution containing bovine serum albumin, labeled with an unconjugated BrdU antibody (EMD Chemicals Inc., Gibbstown, N.J.), and visualized with a fluorescent anti-mouse secondary antibody. Degree of proliferation is determined by counting the number of labeled cells as a percentage of total cells. Degree of proliferation in the presence of the blocking antibody is compared to the degree of proliferation found under the same stimulatory conditions in the absence of the antibody.

EXAMPLE 5

This example demonstrates that an S1P antagonist in accordance with the invention can inhibit the induction of cancer cell migration by S1P. The experiment can first be performed in the absence of the antagonist.

Cell motility is determined using a modified Boyden's chamber assay. MDA-MB-231 cells are introduced into the upper wells of collagen-coated chambers in serum-free DMEM and incubated for 30 minutes before the addition of either 1 μM S1P in BSA or BSA alone. At the indicated times, wells are isolated and fixed with 4% paraformaldehyde before non-migrated cells in the upper well are removed with a cotton swab. Membranes are then stained with DAPI to visualize individual migrated cells on the bottom of the membranes. Results shown are the averages of three independent experiments.

TABLE 5

S1P Induces Cell Migration In Breast Cancer Cells. (Cells/mm$^2$)

|  | 1 hours | 2 hours | 4 hours |
| --- | --- | --- | --- |
| BSA | 387.5 | 465 | 807.5 |
| S1P | 672.5 | 900 | 1385 |

The administration of 1 μM S1P stimulated a rapid and significant increase in cell motility compared to vehicle control. Notably, there is a 74% increase in migrated cells within one hour of S1P administration, which grew to a nearly twofold increase at the two hour time point. When the experiment is performed in the presence of one or more S1P3 antagonist of the invention that increase in cell mobility is diminished or eliminated.

Determination of the effect of S1P3 blocking antibodies on the migration of cancer cells can be performed as follows. The effect of S1P3 blocking antibodies is determined using a modified Boyden chamber assay as described above. In this case, an appropriate cell line (such as MDA-MB-213) is seeded into the upper chamber of the transwell and pre-treated with a blocking antibody or control antibody. Blocking antibodies can be in the form of anti-serum, purified polyclonal antibodies, or purified or unpurified monoclonal antibodies. Control cells are treated with control antibodies that can be in the form of naïve serum, pre-immune serum, purified non-specific polyclonal antibodies, or purified or unpurified non-specific monoclonal antibodies. Following an incubation period (usually 15 minutes to 1 hour) with the antibody or control antibody, cells are stimulated with S1P (usually 1 nM to 10 μM) or with another known pro-migratory stimulus (for example, fetal bovine serum). The stimulatory period varies among the cell lines, but is generally between 1 and 12 hours. Cells are then fixed and counted as described above. The anti-migratory effect of the blocking antibody is determined by comparing the number of migrated cells in the presence of the antibody to the number of migrated cells in the presence of an appropriate control antibody under the same stimulatory conditions.

EXAMPLE 6

This example demonstrates that a S1P antagonist of the invention can sensitize cancer cells to chemotherapy toxicity.

The experiment can be performed first without a S1P antagonist. MDA-MB-231 cells are cultured under standard conditions in Dulbecco's Minimal Essential Media supplemented with 10% fetal bovine serum and glutamate. Cells are grown in the absence of serum for 24 hours prior to experimental manipulation. Tamoxifen (Tam) and S1P are added to the media at the indicated concentrations for the indicated times at the appropriate concentrations (e.g., 3 μM Tam, 10 μM Tam, and 20 μM Tam) for appropriate times (e.g., 6 hrs. and 24 hrs.). Cell viability is observed by direct illumination with an inverted phase contrast microscope.

MDA-MB-231 breast cancer cells cultured under low-density, serum-free conditions are healthy and adherent with visible processes although there are some rounded, dying cells present in the culture. After 6 hours of treatment with 10 μM tamoxifen, only a few viable cells remain and all cells are dead/dying with 20 μM tamoxifen, while many viable cells remain when media is supplemented with 1 μM S1P. Similarly, after a 24 hour treatment, most control cells are lost in the presence of 3 μM tamoxifen and cell death is complete with 10 μM tamoxifen, while the addition of S1P markedly improves survival.

The tamoxifen toxicity experiment can be performed using an antagonist of S1P that binds to S1P3. For example, the antiserum described in Example 1 can be employed. MDA-MB-231 cells are cultured under standard conditions in Dulbecco's Minimal Essential Media supplemented with 10% fetal bovine serum and glutamate. Serum concentration is reduced to 1% for 24 hours prior to experimental manipulation. Tamoxifen and S1P are added to the media at the appropriate concentrations (e.g., 0 μM Tam, 10 μM Tam, and 20 μM Tam) for appropriate times (e.g., 6 hrs. and 24 hrs.). Cell viability is observed by direct illumination with an inverted phase contrast microscope.

Cells treated with Tam for 6 hours in the presence of 1% FBS appear normal at 10 µM Tam and begin to show evidence of cell death at 20 µM. However, co-administration of S1P3 antiserum (1:1,000) greatly enhances the toxicity of Tam with increased cell death at 10 µM, and nearly all cells lost or dying at 20 µM. Similarly, after 24 hours, cell loss and cell death is apparent in the antiserum-treated cells at 5 µM Tam, a concentration that shows no effect on pre-immune serum-treated cells. And at 10 µM, dying cells are present, but most cells remain healthy under control conditions, however, few viable cells remain in the presence of antiserum-containing media.

Quantification of cell death can be performed with an annexin V assay. Serum-starved cells can be treated overnight with 0, 10, or 20 mM tamoxifen in the presence or absence of 500 nM S1P, then collected by trypsinization, and labeled with Alexafluor 488-conjugated annexin V (Invitrogen Corp, Carlsbad, Calif.) per manufacturer's protocol. Cells can be counted on a FACSAria cell sorting system and analyzed with FACSDiva software (BD Biosciences, San Jose, Calif.). Overnight treatment of MCF-7 cells with tamoxifen results in an increase in annexin V binding, signifying an increase in apoptotic cell death. This effect is attenuated by co-administration of 500 nM S1P.

TABLE 6

S1P attenuated tamoxifen-mediated cell death (% Annexin positive cells)

|  | 0 Tamoxifen | 10 µM Tamoxifen | 20 µM Tamoxifen |
|---|---|---|---|
| BSA | 15.4 | 20.1 | 28.9 |
| S1P | 6.2 | 15.9 | 20.2 |

EXAMPLE 7

This example demonstrates monoclonal antibodies that bind to a specific extra-cellular epitope of S1P3.

A synthetic peptide is synthesized with the amino acid sequence: KKTFSLSPTVWFLREG (SEQ ID NO: 1). This sequence corresponds to the extra-cellular loop between transmembrane domains 2 and 3 of cell surface receptor S1P3. This peptide is conjugated to keyhole limpet hemocyanin (KLH) and used for the immunization of 5 balb/c mice. Production of specific antibodies is confirmed by immunocytochemistry. HEK293 cells are transiently transfected with a mammalian expression vector (pcDNA3.1) encoding the full-length S1P3 protein fused to either a V5 epitope or enhanced green fluorescent protein (EGFP) on its C-terminal end. After 16-36 hours, cells are fixed with 4% paraformaldehyde, blocked with BSA, and exposed to antiserum from immunized mice (dilutions of 1:10, 1:25, 1:50, 1:100, 1:250, 1:500, 1:1,000, 1:2,000, 1:5,000), or supernatants from hybridoma cultures. Cells are exposed to antibodies that bind to epitope tags if necessary. Binding of antibodies from serum or supernatants is detected with a Cy3-conjugated secondary antibody. Specificity of binding is evaluated by coincidence of this signal with green fluorescence, either from the expressed EGFP fusion protein or from secondary antibody bound to the expressed V5 epitope.

Mice are immunized with KLH-conjugated peptide at regular intervals and evaluated by enzyme-linked immunosorbent assay (ELISA) and immunocytochemistry until sera are identified that contain specific antibodies (2-3 months). Splenocytes are obtained from mice producing specific antibodies and fused to myeloma cells by polyethylene glycol treatment. Individual hybridoma clones are expanded in 96-well plates. Supernatants from hybridoma cultures are tested for the presence of specific antibodies by immunocytochemistry as described above. 2,496 clones are tested. At least two positive clones are identified and designated "EDDbeta7H9" and "EDDbeta7F6".

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A monoclonal antibody produced from hybridoma MAS 1130 clone 7H9F11 with ATCC accession number PTA-9973 or an antigen-binding fragment thereof.

2. The antigen-binding fragment of claim 1, wherein the antigen-binding fragment comprises a single-chain antibody.

3. A humanized antibody made from the monoclonal antibody or antigen-binding fragment of claim 1.

4. A chimeric antibody comprising the antigen binding fragment of claim 1.

5. An immunoconjugate comprising the monoclonal antibody or antigen-binding fragment thereof of claim 1, which is conjugated to a functional agent.

6. A composition comprising the monoclonal antibody or antigen-binding fragment thereof of claim 1 and a pharmaceutically acceptable excipient.

7. A composition comprising the monoclonal antibody or antigen-binding fragment thereof of claim 1 and an agent selected from the group consisting of an anti-neoplastic agent and an anti-coagulant agent.

8. The composition of claim 7, wherein the anti-neoplastic agent is selected from the group consisting of an estrogen receptor binder, an antimetabolite, a taxane, an anthracycline, progestin, a megestrol, an aromatase inhibitor, an epidermal growth factor inhibitor, any prodrug thereof, any salt thereof, and any combination thereof.

9. A kit comprising the monoclonal antibody or antigen-binding fragment thereof of claim 1.

10. The kit of claim 9, further comprising an anti-neoplastic agent, wherein the anti-neoplastic agent is selected from the group consisting of an estrogen receptor binder, an antimetabolite, a taxane, an anthracycline, progestin, a megestrol, an aromatase inhibitor, an epidermal growth factor inhibitor, any prodrug thereof, any salt thereof, and any combination thereof.

11. A hybridoma having ATCC Deposit Designation PTA-9973.

12. A method of detecting a protein comprising SEQ ID NO:1 in a sample, the method comprising applying the monoclonal antibody or antigen-binding fragment of claim 1, which has been detectably labeled, to said sample and detecting the monoclonal antibody or antigen-binding fragment that binds the protein comprising SEQ ID NO:1.

* * * * *

SEQUENCE LISTING

<160> NUMBER OF SEQ ID NOS: 2

<210> SEQ ID NO 1
<211> LENGTH: 16
<212> TYPE: PRT

```
<213> ORGANISM: Unknown
<220> FEATURE:
<223> OTHER INFORMATION: Description of Unknown: Sphingosine-1-phosphate
      receptor subtype 3 epitope peptide

<400> SEQUENCE: 1

Lys Lys Thr Phe Ser Leu Ser Pro Thr Val Trp Phe Leu Arg Glu Gly
1               5                   10                  15

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(18)
<223> OTHER INFORMATION: This region may encompass 12-18 nucleotides

<400> SEQUENCE: 2
tttttttttt tttttttt                                              18
```